United States Patent [19]

Silberman

[11] Patent Number: 5,178,636
[45] Date of Patent: Jan. 12, 1993

[54] TUNED FRESNEL LENS FOR MULTIFOCAL INTRAOCULAR APPLICATIONS INCLUDING SMALL INCISION SURGERIES

[75] Inventor: Donn M. Silberman, Corona Del Mar, Calif.

[73] Assignee: Iolab Corporation, Claremont, Calif.

[21] Appl. No.: 523,442

[22] Filed: May 14, 1990

[51] Int. Cl.⁵ .................................................. A61F 2/16
[52] U.S. Cl. ........................................ 623/6; 351/161; 359/565
[58] Field of Search ..................... 623/6; 350/162.16; 351/161; 359/565

[56] References Cited

U.S. PATENT DOCUMENTS

| | | | |
|---|---|---|---|
| 4,210,391 | 7/1980 | Cohen | 350/162.16 |
| 4,932,970 | 6/1990 | Portnoy | 623/6 |
| 4,995,714 | 2/1991 | Cohen | 350/162.16 |

FOREIGN PATENT DOCUMENTS 0343067 11/1989 European Pat. Off. ............ 351/161
8902251 3/1989 World Int. Prop. O. ............ 623/6

*Primary Examiner*—Randy C. Shay
*Attorney, Agent, or Firm*—Joel R. Petrow

[57] ABSTRACT

Vision correcting lenses utilizing the principles of both Fresnel lenses and Fresnel zone plates are disclosed. The lenses of the present invention provide multifocal vision correction, and are most preferably used to provide intraocular lenses for small incision surgeries. Using the concept of a "tuned" Fresnel lens, intraocular and other types of vision correcting lenses are provided by the present invention which overcome the limitations found in typical Fresnel lenses by phase synchronizing the light passing through the lens. As disclosed, the groove width and depth of the lens may be varied to provide the synchronization, and also to provide multifocal vision. Also, the design of the present invention permits a relatively thin lens to be designed, therefore making it particularly applicable to small incision surgeries since it may be rolled or folded into a configuration which is easily inserted into an incision in the eye.

10 Claims, 4 Drawing Sheets

TUNED FRESNEL LENS FOR MULTIFOCAL INTRAOCULAR APPLICATIONS INCLUDING SMALL INCISION SURGERIES

The present invention relates to vision correcting lenses and, more specifically relates to multifocal intraocular lenses.

BACKGROUND OF THE INVENTION

For treatment of conditions such as natural eye lens cataracts, a typical eye surgery procedure requires removal of the cataracted lens through an incision in the wall of the cornea of the eyeball, and replacement with an artificial intraocular lens (IOL) as an internal implant lens. Intraocular lenses can be made of a flexible material which permits a reduction of their overall apparent girth by temporary deformation, facilitating their insertion through the cornea, thereby advantageously enabling the use of a corneal incision of concomitantly reduced size. See, e.g., U.S. Pat. No. 4,828,558—Kelman.

A Fresnel lens is normally described by starting with a standard refractive lens, for example the planoconvex lens 10 shown in FIG. 1A, and dividing it into circular zones as shown in FIGS. 1B-1C. These zones each have some of the extra thickness between the plano side of the lens and the convex side of the lens removed, as shown in FIG. 1B. Grooves are left behind, which, for manufacturing considerations, might be made up of flat surfaces to replace the convex portion of the standard lens 10. Normally, inferior image forming capabilities result, and therefore intraocular lenses (IOL's) using this type of lens have not been pursued to a great extent. Referring to FIG. 2, it can be seen that collimated light rays passing through a Fresnel lens converge at a focus point 110, but also exhibit a formation of a large blur "spot," as shown by the arrows, which is undesirable.

Others have attempted to provide vision correcting lenses have the above described unique properties. For example, U.S. Pat. No. 4,637,697—Freeman discloses multifocal contact lenses utilizing diffraction and refraction. Among the embodiments disclosed is one using a Fresnel Zone Plate as an optic element. As explained therein however, the Fresnel Zone Plate should not be confused with the Fresnel Lens, which has no diffractive power. The Fresnel Lens has facetted zones which have random equivalent phase differences between them. This is due largely to having actual phase differences, which are equal to about 100 wavelengths, so that the equivalent residual phase difference may be any value between 0 and $2\pi$ because of random inaccuracies in the manufacturing method. Any amplitude addition across the lens is insignificant and no usable diffractive power is generated. The power of a Fresnel Lens is therefore determined solely by refraction at each of the facets of the lens, each of which forms an image of the object. With correct design these images are formed in the same place and final intensity of the image is found by adding the intensities of the component images.

U.S. Pat. No. 4,828,558—Kelman discloses a laminated optic with an interior Fresnel Lens surface. The Kelman patent discloses the use of a Fresnel Lens which is laminated to entrap gas between the steps or ridges on the surface of the lens. The reference points out that an unlaminated Fresnel Lens, once inserted into the eye, is surrounded by the aqueous humor which coats the exterior of the Fresnel Lens and detracts from its optical effectiveness. The reason set forth in the Kelman reference is that the aqueous humor has an index of refraction sufficiently close to the index of refraction of the intraocular lens material such that the optical characteristics of the Fresnel Lens are detrimentally offset. Thus, this reference teaches that the surface of the Fresnel Lens must be covered by at least a flat planar laminating surface or, alternatively two Fresnel Lens must be placed "ridge to ridge" to protect the ridges and entrap gases therebetween.

It has been found that a "tuned" Fresnel lens operates in a similar manner to a blazed diffraction grating by combining the refraction of the standard Fresnel lens with the coherent superposition of waves of the Fresnel zone plate. See, Vannucci, G., "A 'Tuned' Fresnel Lens", Applied Optics, Vol. 25, No. 16, Aug. 15, 1986, which is incorporated in its entirety herein by reference. A standard Fresnel lens has its spot size, $d_S$, limited by and equal to the groove width, d. This is true in the limited case where, $d^2 >> 2F\lambda$, and diffraction effects are not considered, where F is the focal length of the lens and $\lambda$ is the wavelength of light under consideration. When Fraunhofer Diffraction Theory is considered for the case where $d^2 > 2F\lambda$, then the spot size is $d_S = 2F\lambda/d$. The intensity profile, $I(\rho)$, of the spot is then calculated based on the radial distance, $\rho$, from the center of the spot and the initial intensity, $I_0$, incident on the lens, thus:

$$I(\rho) = \frac{I_0 F\lambda}{\pi^3 d\rho^3} \sin^2 \frac{d\rho\pi}{F\lambda}$$

For the intermediate case where, $d \approx 2F\lambda$, the spot size is determined by the Fresnel Diffraction Theory, a good approximation of which can be derived by assuming:

$d_s \approx d$ when $d^2 \geq 2F\lambda$ $d_s \approx 2F\lambda/d$ when $d^2 \leq 2F\lambda$.

Therefore, optimization of lens performance at a given wavelength is achieved by choosing a groove width, d, that results in the smallest spot size.

In the preceding discussion it has been assumed that for Fresnel lenses in general, light rays from individual grooves are superimposed incoherently at the focal point. This is because the spot diameter from a single groove is the same as the spot diameter from the whole lens. If, however, the groove depth is an integral number of wavelengths in the lens material, then the light emerges from the flat side of the lens in a coherent manner as shown in FIG. 3. The light will therefore focus in a much smaller spot, known as the diffraction limit for the lens diameter, which is the same limit of a conventional lens.

Therefore, it would be desirable to provide a vision correcting lens which utilizes the principles of a Fresnel Lens as well as a Fresnel Zone Plate. Moreover, it would be desirable to provide a Fresnel Lens which may be made of a single layer of material, thereby facilitating insertion into the eye in the form of an intraocular lens. It would be further desirable to provide a Fresnel multifocal intraocular small incision lens which utilizes the principles of Fresnel diffraction theory to facilitate its being "tuned" to provide two or more focal lengths at one or more wavelengths of light.

SUMMARY OF THE INVENTION

The theory of a "tuned" Fresnel lens can now be applied to multifocal intraocular small incision lenses. The present invention provides a lens having alternately varying groove widths and depths to facilitate two or more focal lengths, and preferably at three wavelengths, (red, green, and blue). The numerical design disclosed also provides correction for the appropriate indices of refraction for the medium and the lens material. The present invention thus provides lenses for correcting vision, at least one optical element of which comprises a Fresnel lens which has been "tuned" as set forth above. Specifically, at least two of the grooves within the Fresnel lens are phase synchronized at a particular wavelength of light, whereby the light emerging from the phase synchronized grooves is focused coherently at a focal point. In a most preferred embodiment the lens of the present invention is an intraocular lens for insertion through a small incision in the eye. The present invention also contemplates other applications of the lenses disclosed, such as for a contact lens which is placed on the surface of an eye.

Most preferably, the lenses of the present invention comprise more than one set of grooves which are phase synchronized at more than one wavelength of light. Thus, multifocal applications are disclosed, including embodiments which account for chromatic aberrations. In such multifocal applications, the lens divides the light passing through it and provides at least two foci for said light. Thus, a first portion of the light is focused at a first point for near vision and a second portion of the light is focused at a second focal point for distance vision. This is most preferably accomplished by alternating groove widths on the surface of the lens.

In a most preferred embodiment an intraocular lens for insertion through a small incision in the eye provided which comprise a unitary optic, formed by a relatively thin, sheet-like element comprising a Fresnel lens defining a discontinuous surface formation including a concentric series of grooves. At least two of the grooves are phase synchronized at a particular wavelength of light, whereby the light emerging from the phase synchronized grooves is focused coherently at a focal point. It is therefore understood that in order to accommodate insertion through an incision lenses made in accordance with the most preferred embodiment will be comprised of a flexible, temporarily deformable material. In order to facilitate the numerical design, it is also preferred that the material from which the lens is comprised have a selective index of refraction. Lenses of the type contemplated by the present invention most typically have a thickness of about 1.0-1.5 mm and a diameter of 6 mm. or less.

DETAILED DESCRIPTION

Figure 1A:
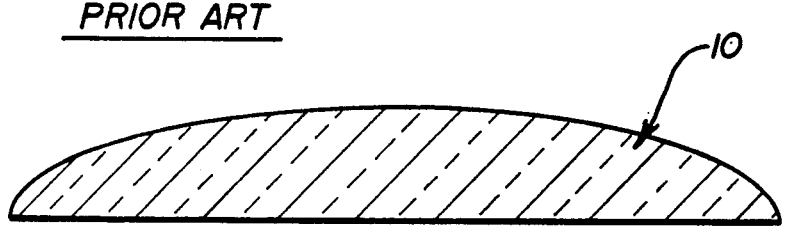
FIG. 1A depicts a cross-sectional view of a conventional prior act plano convex lens.
Figure 1B:
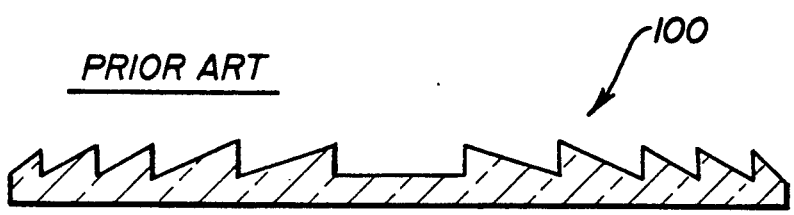
FIG. 1B depicts a cross-sectional view of a prior art Fresnel lens which is optically similar to that of FIG. 1A.
Figure 1C:
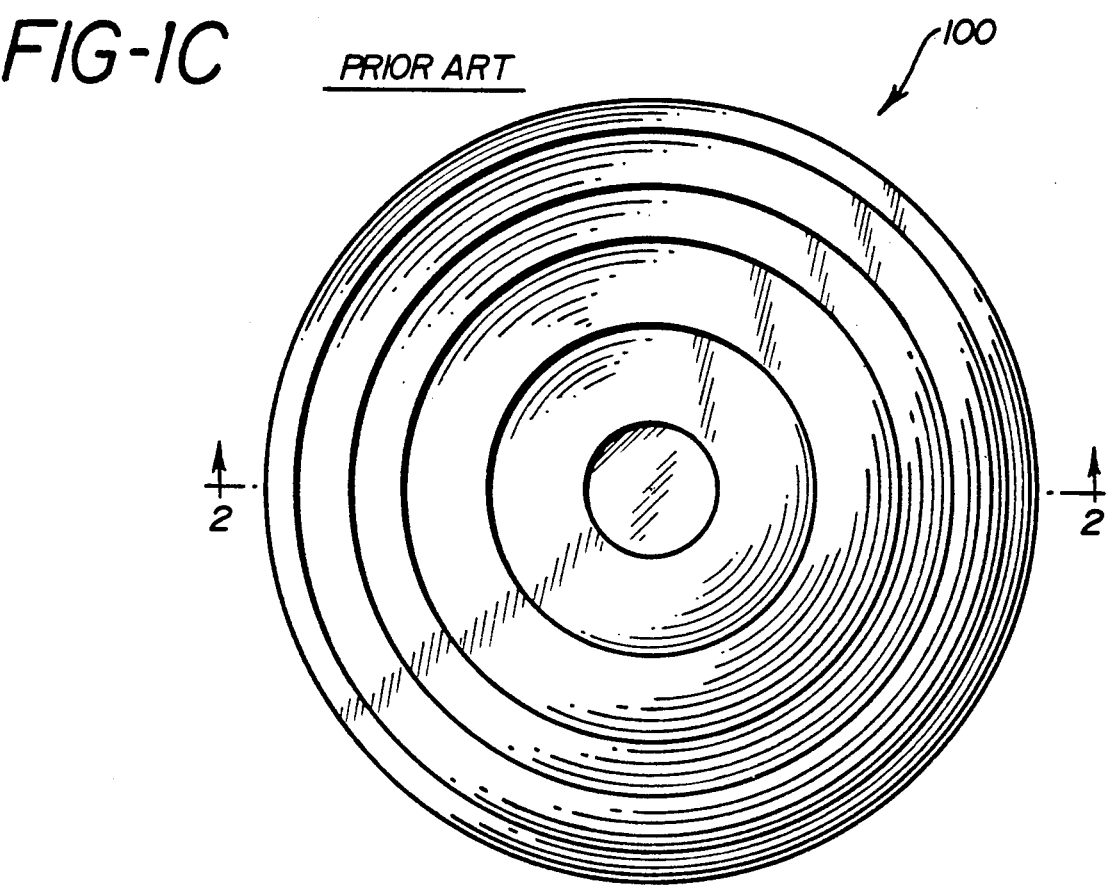
FIG. 1C is a top plan view of the lens shown in FIG. 1B.

Referring to FIGS. 1A–1C, as explained above, a conventional plano convex lens 10 can be sliced into thin cylindrical sections, as shown. A Fresnel lens 100 which is effectively a flat array of thin annular lenses may then be formed, as shown in FIGS. 1B and 1C this lens 100 is therefore substantially the optical equivalent of the lens 10 shown in FIG. 1A.

Figure 2:
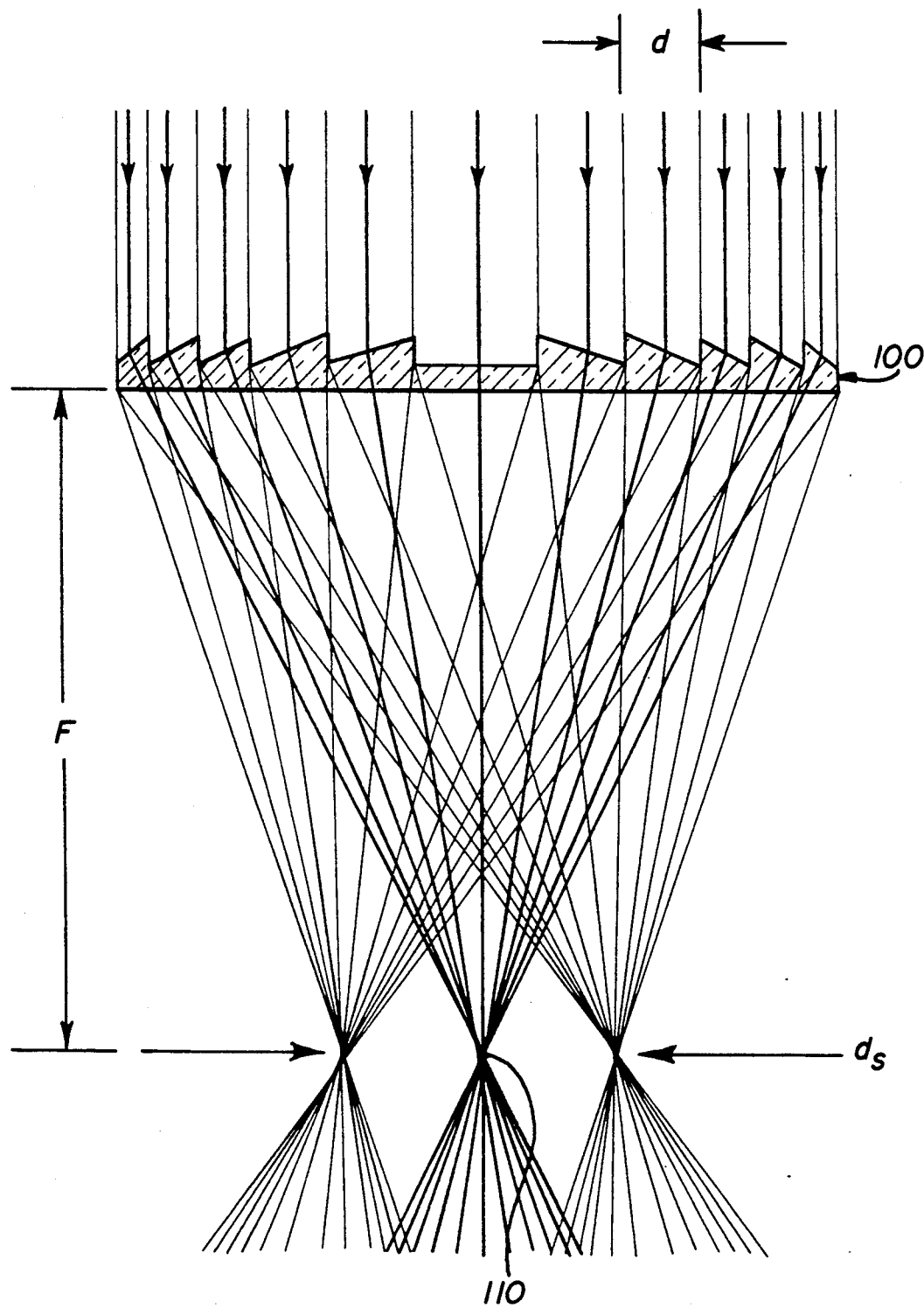
FIG. 2 shows the geometry of collimated light rays passing through the lens of FIG. 1B.

As shown in FIG. 2, as light rays from a collimated source (not shown) pass through the lens 100 they are focused at a focal point 110.

As demonstrated in the equation set forth above, the optimum value for a groove width, d, which achieves the smallest spot size is:

$$d = \sqrt{2F\lambda}$$

which corresponds to a spot diameter:

$$d_s \approx \sqrt{2F\lambda}$$

One of ordinary skill will observe that the best angular resolutions if the lens is used for imaging or spatial filtering is:

$$\frac{d_s}{F} = \sqrt{\frac{2\lambda}{F}}$$

Angular resolution thus improves proportionally to the square root of the focal length. In a conventional lens, on the other hand, angular resolution is the diffraction limit for a given aperture size and therefore depends only upon lens diameter without regard to focal length.

Figure 3:
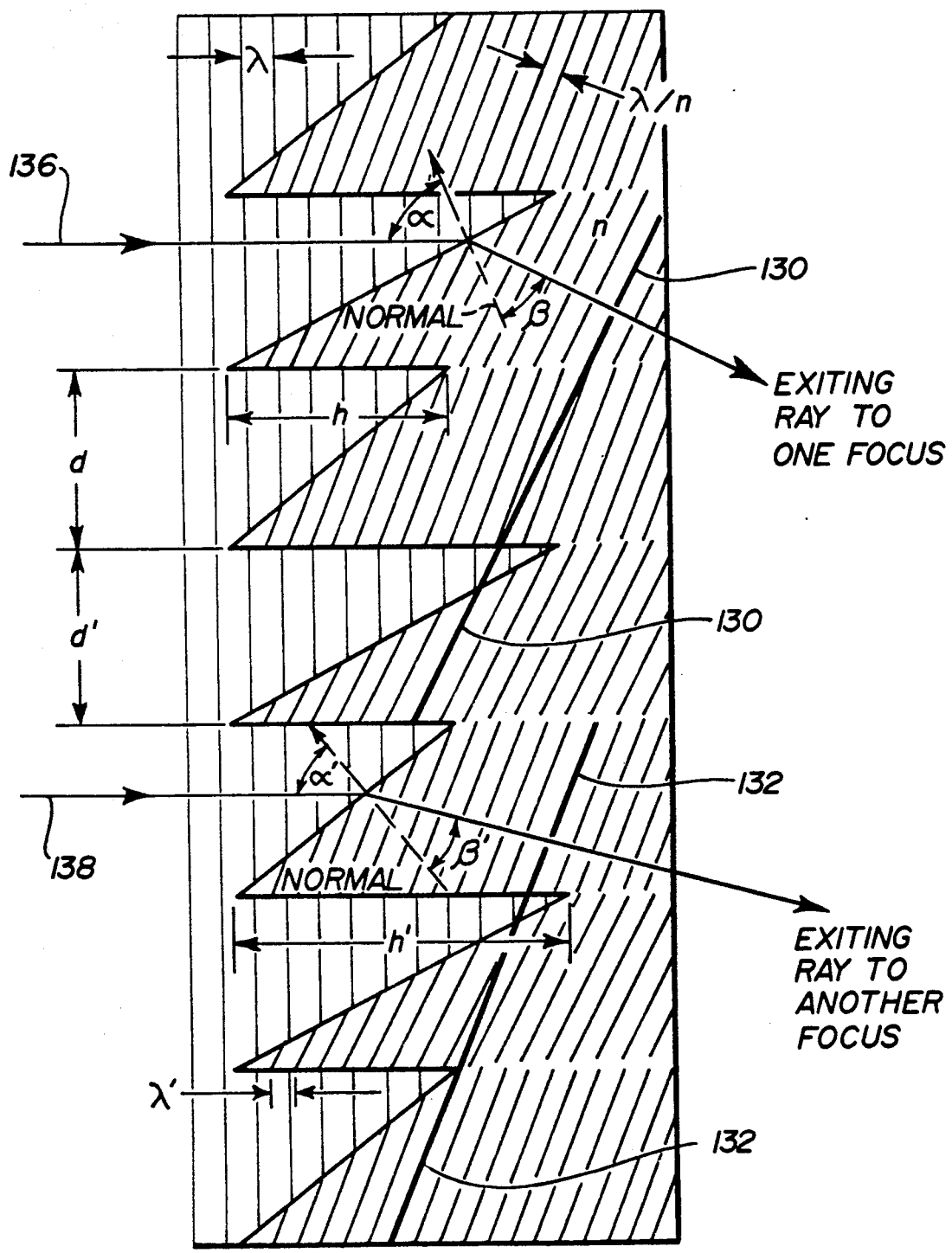
FIG. 3 partial cross-sectional view depicts the passage of wave fronts through a section of a tuned Fresnel lens made in accordance with the present invention.

A portion of a cross-section of a tuned Fresnel lens made in accordance with the present invention is shown in FIG. 3. As explained above, in the usual case the light rays passing through the individual grooves are superposed incoherently at the focal point. This is implicit in the assumption that the spot diameter due to a single groove is the same as the spot diameter achieved by the entire lens. However, as shown diagrammatically in FIG. 3, if the depth of the grooves, h and h' are chosen to superimpose the wave fronts 130, 132 coherently at the focal points, the lens performance can be substantially improved over that of a standard Fresnel lens.

Thus, it has now been found that coherent superposition can be achieved at a given wavelength for wave fronts emanating from a point source located on the lens axis at a given distance from the lens. If the light is assumed to be a point source located at infinity, the incoming plane wave fronts 136, 138 will be perpendicular to the lens axis. By creating a "tuned" Fresnel lens for this case, the principles of conventional Fresnel lenses and Fresnel zone plates are effectively and advantageously combined.

As shown in FIG. 3, the depth of the grooves is chosen to result in the wave fronts emerging from two adjacent grooves being exactly in phase. As the wave fronts enter the material of a lens made in accordance with the present invention, they are refracted according to Snell's law of refraction:

$$\frac{\sin\alpha}{\sin\beta} = n$$

where the angles $\alpha$ and $\beta$ are the angles of incidence and refraction respectively, as shown in FIG. 3, and n is the index of refraction of the material. The distance between wave fronts prior to entering the lens is $\lambda$; the distance between wave fronts inside the material of the lens is, $\lambda'$, is:

$$\lambda' = \lambda \frac{\sin\beta}{\sin\alpha\cos(\alpha - \beta)} = \frac{\lambda}{n\cos(\alpha - \beta)}$$

It can be seen that for a groove of depth h, the phase difference between the waves going through adjacent grooves will be:

$$\Delta\phi = 2\pi h \left(\frac{1}{\lambda'} - \frac{1}{\lambda}\right)$$

$$= 2\pi \frac{h}{\lambda} [n\cos(\alpha - \beta) - 1]$$

Since $\Delta\phi$ must be an integer multiple of $2\pi$ for coherent superposition, h must therefore be an integer multiple of:

$$\lambda = \frac{\lambda}{[n\cos(\alpha - \beta) - 1]}$$

EXAMPLE I

Figure 4:
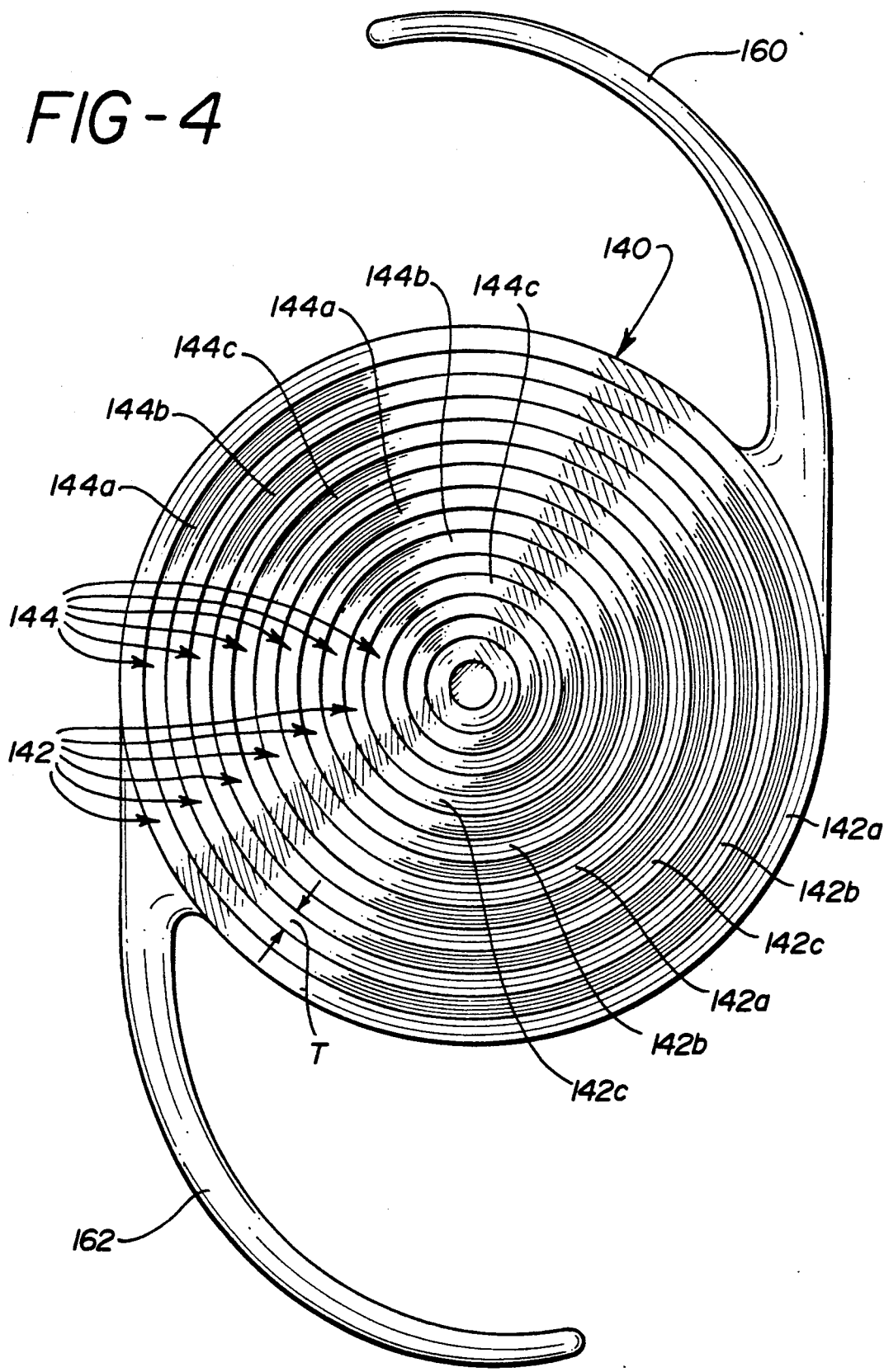
FIG. 4 is a top plan view of an intraocular lens incorporating the present invention.

Referring to FIG. 4, typical flexible IOL 140 has a diameter of about 6.00 mm and a focal length (in air) of 23 mm the radius of curvature, R1 will be 10 mm when the refractive index of the IOL is 1.43. This lens will then have an optical power in aqueous, Daq, of about 9.5D. An IOL of the same material, and with optical power 4.0D greater than the previously discussed 9.5D IOL will have a focal length (in air) of 16.2 mm and a radius of curvature, R2, of 6.962 mm. Combining the optical powers of these two lenses into one multifocal tuned Fresnel IOL is shown in general terms using small angle approximations.

An arbitrary groove width, T, of 0.25 mm is chosen for this example. The normal Fresnel groove depth, $d_i = T X_1/R_j$, where $X_i$ is the radial distance to the center of the ith groove. This is then divided by $\lambda(n-1)$ to determine the integer, N, which will be used to determine the tuned groove depth, $h_1 = N \lambda (n-1)$. The fifth groove has $X_5 = 1.125$ mm, $R_1 = 10$ mm, $d_5 = 28.125$ mm, $N = 119$, $\lambda = 0.55$ $\mu$m, and $h_5 = 28.1435$ $\mu$m. The sixth groove has $X_6 = 1.375$ mm, $R_2 = 6.962$ mm, $d_6 = 49.3625$ $\mu$m, $N = 209$, $\lambda = 0.55$ $\mu$m, and $h_6 = 49.4285$ $\mu$m. Therefore, the condition that the groove depth be in integer multiple of $\lambda$ can be met without altering the basic structure of the lens. The nominal depth of the individual grooves must be modified only by a small percentage to achieve the desired result.

The performance of a tuned Fresnel lens for correcting vision made in accordance with the present invention can be as good as that of a conventional lens of the same diameter. A lens made in the manner disclosed herein can achieve the diffraction limit for its aperture size. This is an important consideration when considering the characteristics of a lens for use in an ophthalmic application. Typical diffractive lenses exhibit about a 20% light loss, while a lens made in accordance with the present invention exhibits approximately the same transmissivity as a conventional lens.

As will be understood by those of ordinary optical design skill, the lens design methodology set forth above can be utilized to provide single focus or multifocal lenses. In the latter applications, the second and other foci may be provided either by using the principles of the present invention or by using a lens as disclosed above in conjunction with other more conventional designs. The latter could comprise either a laminated or composite structure utilizing diffractive or refractive principles to generate a second focal point. Alternatively, volume and/or surface holograms may be incorporated into a multi-focal lens design.

For multifocal applications, two or more sets of phase synchronized grooves may be formed in the surface of the lens. Bifocal vision can be provided by two sets of grooves 142, 144 which are phase synchronized to provide two foci, one for distance vision and one for near vision. By providing grooves focused at distinct wavelengths 142a, 142b, 142c, 144a, 144b, 144c within the visible spectrum, chromatic aberrations and other visual problems can be improved along with the provision of bifocal vision. Most preferably, the lens is designed for wavelengths at about 650 nm, 550 nm and 450 nm, corresponding to red, green and blue light.

As set forth above, the lens design of the present invention requires alterations of the groove sizes. Lenses made in accordance with this invention can be efficiently manufactured by molding or other known processes. The optical benefits of this design are therefore achieved without a significant impact on the unit cost.

In certain embodiments intraocular lenses are also provided with haptics of flexible, temporarily deformable material. These haptics aid in the placement and orientation of the lens within the eye.

Although certain embodiments and an Example of the present invention have been set forth with particularity, these are not intended to limit the scope of the present invention. Numerous variations and modifications within the spirit of the invention will present themselves to those of ordinary skill. Accordingly, reference should be made to the appended claims to determine the scope of the present invention.

What is claimed is:

1. A multifocal lens for correcting vision comprising a Fresnel lens having a first set of grooves to provide a first light focal point, and a second set of grooves to provide a second light focal point, wherein at least one of the groove within each set of grooves is phase synchronized with another groove in the set to which it belongs at a first wavelength of light for that set such that the light at the first wavelengths for each set, respectively emerging from said phase synchronized grooves contained within each set of grooves is focused coherently at said first and said second focal points, respectively.

2. The lens of claim 1, wherein said lens is an intraocular lens for insertion through an incision in the eye.

3. The lens of claims 1, wherein said lens is a contact lens for placement on the surface of the eye.

4. The lens of claim 1, said first and second sets of grooves each further comprising at least one groove which is phase synchronized with another groove in the set to which it belongs at a second wavelength of light distinct from said first wavelength for each set such that the light at said respective second wavelength emerging from said phase synchronized grooves contained within each said set of grooves is focused coherently at said first and said second focal points, respectively.

5. The lens of claim 4, said first and second sets of grooves each further comprising at least one groove which is phase synchronized with another groove in the set to which it belongs at a third wavelength of light distinct from said first and second wavelengths for each set such that the light at said respective third wavelengths emerging from said phase synchronized grooves contained within each said set of grooves is focused coherently at said first and said second focal points, respectively.

6. The lens of claim 5, wherein said first, second, and third wavelengths of light lie within the visible light spectrum.

7. The lens of claim 6 wherein a first of said three wavelengths is about 650 nm, a second is about 550 nm and a third is about 450 nm.

8. The lens of claim 1 comprising two or more alternating groove widths.

9. The lens of claim 1, wherein the measured diameter of said focal point is equal to about $$\sqrt{2F\lambda},$$

wherein F is the focal length of the lens and $\lambda$ is the design wavelength of the light.

10. The lens of claim 1, wherein the depth of said grooves is an integer multiple of $$\frac{\lambda}{[n\cos(\alpha - \beta) - 1]}$$

where (lens in air) $\lambda$ is the wavelength of the light, n is the index of refraction of the lens material, $\alpha$ is the angle of incidence of the light and $\beta$ is the angle of refraction.

* * * * *

UNITED STATES PATENT AND TRADEMARK OFFICE
CERTIFICATE OF CORRECTION

PATENT NO. : 5,178,636

DATED : January 12, 1993

INVENTOR(S) : Donn M. Silberman

It is certified that error appears in the above-identified patent and that said Letters Patent is hereby corrected as shown below:

In claim 1, column 6, line 52, the word "groove" should read "grooves"

In claim 10, column 8, line 18, the number "10" should be deleted

Signed and Sealed this

Twelfth Day of July, 1994

Attest:

BRUCE LEHMAN

Attesting Officer    Commissioner of Patents and Trademarks